(12) United States Patent
Bodenstein

(10) Patent No.: US 8,282,545 B1
(45) Date of Patent: Oct. 9, 2012

(54) INTRA-CORPOREAL SURGICAL RETRACTOR

(76) Inventor: Lawrence Bodenstein, Bronx, NY (US)

(*) Notice: Subject to any disclaimer, the term of this patent is extended or adjusted under 35 U.S.C. 154(b) by 1369 days.

(21) Appl. No.: 11/809,348

(22) Filed: May 31, 2007

Related U.S. Application Data

(63) Continuation-in-part of application No. 10/167,350, filed on Jun. 11, 2002, now abandoned.

(60) Provisional application No. 60/377,682, filed on May 4, 2002.

(51) Int. Cl.
*A61B 1/32* (2006.01)

(52) U.S. Cl. ........................................ 600/206; 600/205

(58) Field of Classification Search .......... 600/201–246; 604/509, 95.03, 96.01, 101.01–101.05, 103, 604/103.05, 103.07
See application file for complete search history.

(56) References Cited

U.S. PATENT DOCUMENTS

| | | | | |
|---|---|---|---|---|
| 3,212,497 A | * | 10/1965 | Dickinson | 602/6 |
| 3,745,998 A | * | 7/1973 | Rose | 602/6 |
| 3,892,314 A | * | 7/1975 | Semp | 206/363 |
| 4,533,356 A | * | 8/1985 | Bengmark et al. | 604/358 |
| 4,848,364 A | * | 7/1989 | Bosman | 128/849 |
| 4,974,725 A | * | 12/1990 | Ishihara et al. | 206/0.5 |
| 5,159,921 A | * | 11/1992 | Hoover | 600/207 |
| 6,036,641 A | * | 3/2000 | Taylor et al. | 600/231 |
| 6,251,065 B1 | * | 6/2001 | Kochamba et al. | 600/37 |
| 6,656,488 B2 | * | 12/2003 | Yi et al. | 424/423 |
| 2003/0055378 A1 | * | 3/2003 | Wang et al. | 604/103.07 |

* cited by examiner

*Primary Examiner* — Kevin T Truong
*Assistant Examiner* — Larry E Waggle, Jr.
(74) *Attorney, Agent, or Firm* — Levisohn Berger LLP

(57) ABSTRACT

An intra-corporeal surgical retractor for holding tissues and organs in place is provided, including a sealed container, made from a flexible material, having an interior containing a granular substance and a fluid. At least one tube may be provided with one end attached to the container in communication with the interior of the container and the other end connected to a suction mechanism. When the fluid is evacuated from the container, the container constricts around the granular substance and becomes relatively rigid. An absorbent sleeve or layer may be provided surrounding the container. The granular substance may be provided as loose fill or as a layer over at least a portion of the inner wall. Alternatively, the inner walls of the container may be provided with a very rough surface. Further, the outer surface of the bottom of the pouch is enhanced frictionally.

12 Claims, 1 Drawing Sheet

INTRA-CORPOREAL SURGICAL RETRACTOR

RELATED APPLICATIONS

This application claims domestic priority from U.S. Provisional Patent Application No. 60/377,682, filed on May 4, 2002 and is a continuation-in-part of U.S. Non-Provisional patent application Ser. No. 10/167,350, filed on Jun. 11, 2002 and incorporates all of the teachings therein here by reference.

BACKGROUND OF THE INVENTION

1. Field of the Invention

The invention relates to surgical devices, and more specifically to surgical retractors for displacing organs and tissues and maintaining them in a specific position in a surgical environment.

2. Description of the Related Art

During surgery, a physician will typically work on a small area or portion of a patient and will need to push the organs and tissues that are not being treated away from the area in question. Alternatively, a physician may need to treat the underside of an organ (or another inconvenient or difficult to reach surface or section) and will need to prop it up for an extended period of time. Surgeons employ several different means of maneuvering organs and other body parts away from a surgical site and keeping them out of their way.

One common method uses common gauze or sponges. The surgeon essentially props up a neighboring organ with a wad of gauze or a sponge to keep the organ out of her field. This method has several drawbacks. First, surgical sponges and gauze are extremely flexible and pliant and do not offer much resistance. As a result, the organ or tissue has a tendency to flop over or push the sponge or gauze out of the way. Additionally, sponges and gauze are difficult to position or mold properly in the first place. Also, as their name suggests, sponges are extremely absorbent. Since the field is filled with bodily fluids, the sponges are constantly absorbing those fluids, which has a deleterious effect on the sponges' rigidity and ability to keep back the organ or tissue.

U.S. Pat. Nos. 6,254,534 to Butler et al., 6,142,936 to Beane et al., and 5,159,921 to Hoover describe tubular-shaped retractors which laterally pull apart a wound opening for access into the field. These patents are silent as to the shifting of organs or blood vessels within the field, i.e., they do not teach or suggest an intra-corporeal retractor at all. U.S. Pat. No. 6,090,041 to Clark et al. describes a vacuum-actuated retractor for retracting body tissue during surgical procedures. One end of the retractor is adapted to seal with a body tissue such that a suction force is applied to the body tissue when the device is activated. A detriment to Clark's device is that the device cannot be molded to fit a specific irregular space or retain a variety of different structures as it is non-malleable. There is also a potential risk of injuring the tissue by application of the vacuum suction.

U.S. Pat. No. 5,460,621 to Gertzman et al. describes a composite tissue displacement sponge having multiple layers of rigid, compressed, absorbent poly vinyl acetate material. The sponge may be compressed into a rigid and dry form which allows the sponge to conform to a precise space of the cavity or site required for organ displacement or protection. The sponge may be hydrated to expand it. This device works suitably as a sponge, however it fails as a retractor that does not react at all with the organs or tissues it retains, because it is constantly absorbing fluid.

U.S. Pat. No. 4,889,107 to Kaufman describes a surgical retractor having a non-absorbent barrier member surrounding a malleable but shape-retaining core.

All of the above references teach devices which cannot be used with minimally invasive surgical procedures (e.g., laparoscopy, retroperitoneoscopy, thoroscopy) and are limited in their ability to be molded into a specific shape.

SUMMARY OF THE INVENTION

It is an object of the invention to provide a surgical retractor or tissue displacement device which can be used readily in a variety of surgical applications.

It is another object of the invention to provide a surgical retractor or tissue displacement device which is completely non-reactive to the organs or tissues it is retaining or displacing.

It is another object of the invention to provide a surgical retractor or tissue displacement device which can be used in both minimally invasive and conventional surgical situations.

The above and other objects are fulfilled by the invention.

One embodiment of the invention is a tissue displacement surgical retractor, which includes a sealed container, made from a flexible material, having an interior containing a granular substance and a fluid (e.g., a gas). At least one tube is provided with one end attached to the container in communication with the interior of the container and the other end connected to a suction mechanism. The surgical retractor is placed on a body site. Since the sealed container is a flexible material the retractor can easily conform to the body site and readily form a bottom surface which sits on the body site. When the fluid is evacuated from the container, the container constricts around the granular substance and becomes relatively rigid. The device is first molded around the tissue or organ with the tissue or organ in the desired position. The fluid (e.g., air) is evacuated, and the device retains its shape. The granular substance comprises sufficient ballast or weight so that it remains in place where positioned at the body site to perform the retraction functions. As a result, the organ or tissue is retained in place. An absorbent sleeve or layer may be provided surrounding the container.

The granular substance is preferably substantially incompressible; it may be provided as loose fill or as a layer over at least a portion of the inner wall. If provided as loose fill, the granular substance is preferably a biologically compatible material safely absorbable by the human body. The first end of the tube preferably includes a filter to prevent the granular substance from being evacuated along with the fluid. If provided in a layer over at least a portion of the inner wall, the granular substance prevents the slippage of one wall of the container against the other, and the device retains its shape.

In one embodiment, the sealed container includes at least one interior separating wall dividing the interior of the sealed container into at least two compartments. A plurality of tubes may be provided each in communication with a respective compartment. Alternatively, a single tube is provided in communication with one of the compartments and the interior separating walls are fluid permeable, so that the fluid may be evacuated from all of the compartments via the one tube.

Another embodiment of the invention is an intra-corporeal surgical retractor having a sealed container is made from a flexible material being conformable to substantially any desired shape. The container has interior walls having a sufficiently high coefficient of friction so that the interior walls cannot substantially slide against one another when in contact. The specific coefficient of friction may vary depending on the size and configuration of the retractor, however it is readily determinable by one of skill in the art. The container also contains a fluid. At least one tube is provided, one end of which is attached to the container in communication with the interior of the container, the other end of which is connected to a suction mechanism. When the fluid is evacuated from the container, the interior walls of the container compact together and the container becomes relatively rigid and retains its shape and remains in place due to friction and its ballast or weight.

The invention also includes methods of displacing intracorporeal tissue. First, a sealed container having a granular substance and a fluid therein is provided. Next, the sealed container is conformed around the tissue to be displaced or the item to be packed. Finally, the fluid from the sealed container is evacuated, thereby leaving the sealed container in a rigid configuration, either displacing the tissue or organ or retaining the packed item. As before, the granular substance may either be loose fill or provided in a layer on at least a portion of interior walls of the sealed container.

DETAILED DESCRIPTION OF THE INVENTION

Description will now be given with reference to the attached FIGS. 1-4. It should be noted that these figures are merely exemplary in nature and in no way serve to limit the scope of the invention.

Figure 1:
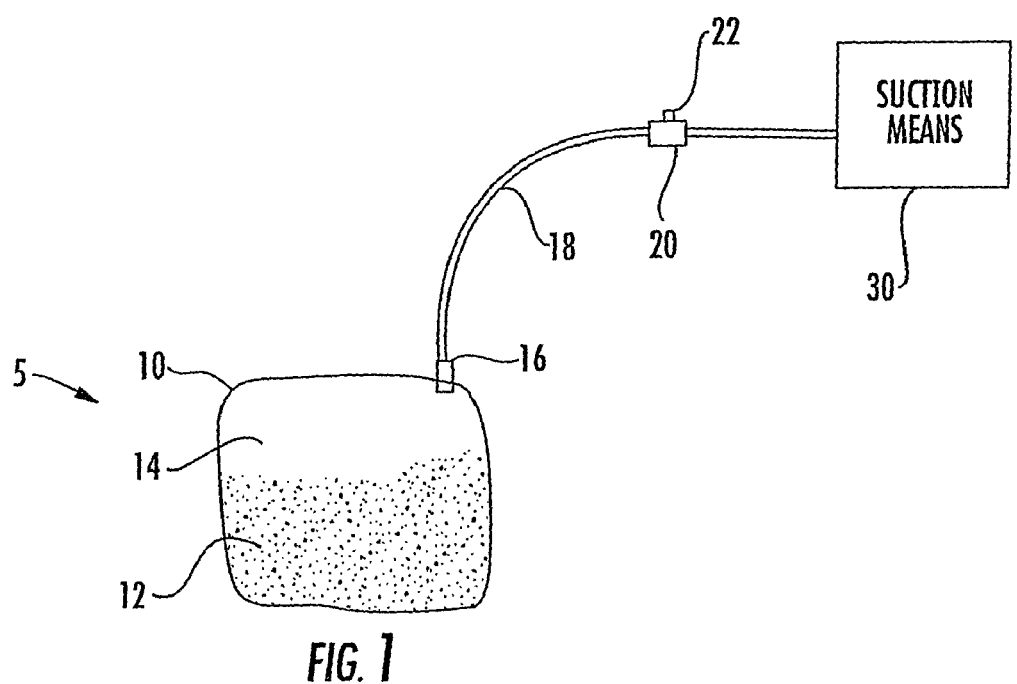
FIG. 1 is a schematic view of a generic embodiment of a device according to the invention.

FIG. 1 illustrates the general concept of the inventive surgical retractor 5. Bag or pouch 10 is made from an inert, non-toxic, pliable plastic or polymer and is at least partially filled with a granular substance 12. The granular substance can be any convenient substance having a consistency similar to that of salt, sugar, sand, or the like. Although pouch 10 will be sealed and impervious to granular substance 12, because pouch 10 might be punctured or torn accidentally (especially during surgery), using a biologically compatible material for granular substance 12 is desirable. Such granular materials may include granular sugar, polyglycolic acid, poliglecaprone 25, granular polydioxanone, or any other material safely absorbable by the human body. In any event, pouch 10 should not be completely filled with granular substance 12; an airspace 14 should be left in the interior of pouch 10. The amount of granular substance 12 used will depend on the specific use. Greater amounts of granular filling provide firmer retraction. Also, the heavier or denser the material to be used is, the more "ballast" it provides, and thus the more positionally stable the device is. Thus, since the pouch 10 is flexible and is filled with granular filling 12 having ballast or weight, the pouch when placed on a body site in the conventional manner conforms to the shape needed and sits on the body site due to its ballast or weight. If the body site is flat, the bottom of the pouch will also be flat as it sits on the body site, and if the body site is irregular, the pouch will sit thereon and conform to the irregular shape before it is rendered stiff. Thus, the pouch independently stays in place due to its own weight at the body site.

Attached at one or more points to pouch 10 and communicating with the interior of pouch 10 is a port or connector 16. Tubing 18 is attached at one end to connector 16. A filter is preferably provided in connector 16 so as to prevent the egress of granular substance 12 from pouch 10 via connector 16. The other end of tubing 18 is connected to a suction means 30. A one-way valve 20 having a release mechanism 22 is disposed along tubing 18. When suction means 30 is activated, it withdraws the air from pouch 10. Since the walls of pouch 10 are pliant, the walls constrict around granular substance 12. Because the valve 20 is one-way, air will be withdrawn from pouch 10 and not be allowed to return until and unless release 22 is depressed.

Suction means 30 may be of several designs, including a hand pump, an electric pump, or a central vacuum line in a building. Depending on which suction means is used, tubing 18 may be permanently connected or selectively connectable to the suction means. If the suction means 30 is a hand pump, tubing 18 may be permanently connected to the hand pump, which may take the form of a syringe, for example. By contrast, if the suction means is a central vacuum line, tubing 18 would be selectively connectable to the central vacuum line and not permanently attached. Alternatively, valve 20 can be provided in direct communication with pouch 10 and adaptable to be connected directly to suction means 30, thereby eliminating the need for tubing 18.

In operation, the invention works as follows. A surgeon operating on a patient wishes to retract or retain certain tissues or organs while working on others. The surgeon places pouch 10 in the desired body site location and molds it manually to a convenient configuration. When pouch 10 is properly configured, the surgeon or his assistant activates the suction means to withdraw the air from pouch 10. The walls of pouch 10 constrict around granular substance 12, and pouch 10 is rigidly fixed into a configuration; the granular substance is not able to shift or move around within pouch 10. The pouch conforms to the body site and stays in place because of its ballast as described above. Device 5 can thus successfully keep tissues or organs out of the surgeon's way while operating. When it is desired to unfix or relax the configuration of pouch 10, the surgeon or his assistant activates valve release 22, and air is allowed to return to pouch 10, and pouch 10 is no longer rigid.

Because device 5 has a non-rigid state, it is well-suited for use in minimally invasive surgery such as laparoscopy. The device can be inserted through a small incision and, once inside the patient, it can be manipulated through the use of tools known in the laparoscopic field.

Figures 2, 3:
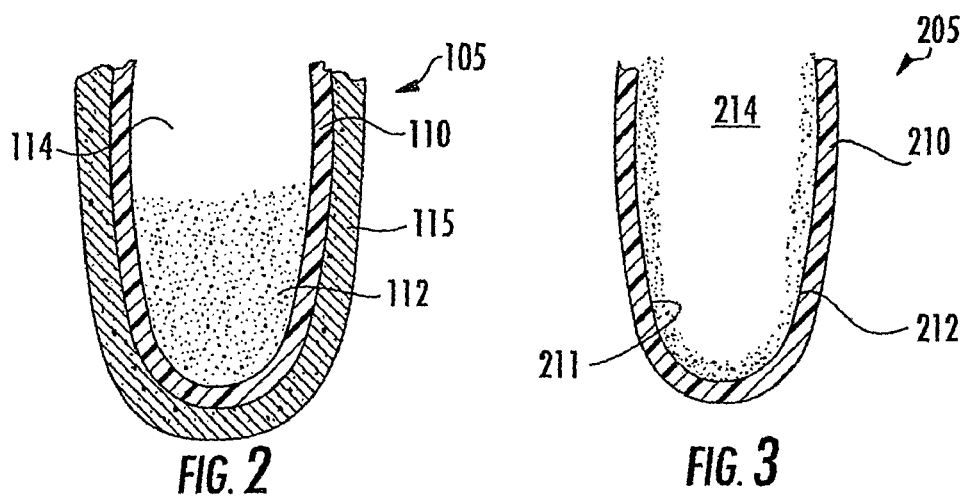
FIG. 2 is a partial sectional view of a first embodiment of a device according to the invention.
FIG. 3 is a partial sectional view of a second embodiment of a device according to the invention.

FIG. 2 depicts a partial sectional view of a first embodiment of the pouch of the invention. Device 105 includes a plastic or polymer pouch 110 having loose granular fill 112 disposed therein. Space 114 is also provided as explained above. The minimum amount of space required in pouch 110 is only enough to allow the granular material 112 to shift and be malleable. Additional space could be provided.

FIG. 3 depicts a partial sectional view of a second embodiment of the invention. Device 205 includes a plastic or polymer pouch 210 as before. However, instead of containing loose granular fill, pouch 210 is provided with a rough or coarse granular surface inner coating 212. Interior 214 of pouch 210 is substantially empty. When the air is evacuated from the pouch, the interior walls 211 of the pouch come into contact with one another, as indicated by arrows A in FIG. 3. The extremely high coefficient of friction between mating inner coating surfaces prevents the pouch 210 from moving or deforming substantially, and pouch 210 becomes rigid. It is also contemplated to provide simply an extremely rough surface that is not necessarily made from a layer of granular material being applied to the interior walls 211 of the pouch 205.

Figure 4:
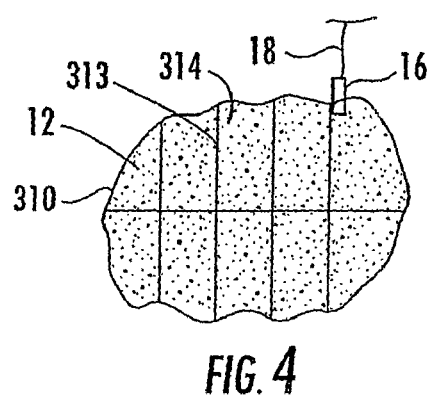
FIG. 4 is a schematic view of a third embodiment of a device according to the invention.

FIG. 4 depicts a partial schematic view of a third embodiment of the invention. Like the first embodiment, pouch 310 contains loose granular material 12. However, the interior of pouch 310 is compartmentalized by the provision of interior separating walls 313. Walls 313 insure that granular material 12 remains evenly distributed throughout the interior of pouch 310. As shown in FIG. 4, a single port 16 is provided. In such an embodiment, walls 313 are preferably air permeable so that the air from all of the compartments 314 can be evacuated via a single port. However, it is also contemplated that walls 313 may be air impermeable; in such an embodiment, each compartment would require its own port for the evacuation of its air. Multiple ports could be connected to multiple tubes 18, which could be either separately controllable via individual valves or all connected to a single valve.

As an additional feature, as shown in FIG. 2, for example, an absorbent sleeve 115 may be provided around the exterior of the pouch to act as a sponge. The sleeve may be integral with the pouch or it may be removable. The provision of this outer absorbent sleeve provides additional cushioning for the supported tissues and provides increased friction to minimize any potential drift of the device within the patient. The sleeve 115 is shown as surrounding pouch 110, however it may be provided with any of the embodiments described above or any other versions of the invention.

The invention is not limited to the above description. For example, the air inside pouch 10 which is withdrawn to fix the device in a specific configuration may be replaced by another gas or a liquid. In such an embodiment, the suction means may also have a pumping function to replace the specific gas to the interior of pouch 10 when it is desired to relax the configuration of the pouch. Also, the invention has been described as suitable for keeping organs and tissues out of the way of the surgeon operating on other tissues or organs, however the invention is also useful for positioning the tissue or organ that is being treated. The device is contemplated as being available in a variety of sizes and shapes (e.g., spherical, toroidal, fenestrated, oblong, irregular, etc.) for a variety of surgical applications.

It is further understood that the retractor stays in place because body sites themselves are not perfect surfaces and the lodging of the retractor in between body parts or on body surfaces may involve wedging into a space or frictional holding because of the nature of the surfaces and tissue. Having the retractor contain sufficient ballast or weight further ensures positional stability.

An additional embodiment is now described. In order to enhance the frictional holding of the retractor on a body surface, the outer surface of the pouch is roughened or comprises an enhanced frictional surface, such as corrugation. The enhanced frictional surface may be primarily on the outer surface at the bottom of the pouch.

The invention is not limited to the above description but rather is defined by the claims appearing hereinbelow. Modifications to the above description that include that which is known in the art are well within the scope of the contemplated invention.

What is claimed is:

1. An intra-corporeal surgical retractor having positional stability for maintaining tissue away from any of a plurality of surgical sites in the body during surgery to stably expose the surgical site permitting improved access thereto, said surgical retractor comprising a free form sealed pouch comprising a fluid impermeable single wall having a pouch shape comprising a flexible material and having an interior space containing a granular substance and a fluid, said single wall free form pouch being essentially formless and comprising an inert pliant plastic material shapeable and deformable in any direction to form a structural barrier and maintain said tissue away from said surgical site said pouch placed near the surgical site to form said structural barrier, means for enabling evacuation of said fluid, said granular substance located in said interior space directly bearing against the inner walls of said impermeable single wall pouch, when said fluid is evacuated from said pouch, said pouch constricts around said granular substance in said interior space to form said structural barrier to have a shape defined by the granular substance bearing directly against the inner wall, said structural barrier becoming relatively rigid to stay in place with positional stability at said body site, said relatively rigid pouch having sufficient rigidity and positional stability to move and maintain said tissue away from said surgical site.

2. An intra-corporeal surgical retractor according to claim 1, wherein said body site comprises flat surfaces and said pouch rests on said flat surfaces conforming thereto.

3. An intra-corporeal surgical retractor according to claim 1, further comprising:
   at least one tube having a first end and a second end, said first end attached to said pouch in communication with said interior or said pouch, said second end connected to a suction mechanism.

4. An intra-corporeal surgical retractor according to claim 1, said granular substance being substantially incompressible.

5. An intra-corporeal surgical retractor according to claim 1, said granular substance being provided as loose fill.

6. An intra-corporeal surgical retractor according to claim 5, said granular substance being a biologically compatible material safely absorbable by the human body.

7. An intra-corporeal surgical retractor according to claim 6, said granular substance being comprised of at least one of granular sugar, polyglycolic acid, poliglecaprone 25, and granular polydioxanone.

8. An intra-corporeal surgical retractor according to claim 3, wherein said first end of said tube comprises a filter to prevent said granular substance from being evacuated along with said fluid.

9. An intra-corporeal surgical retractor according to claim 1, wherein said fluid is air.

10. An intra-corporeal surgical retractor according to claim 3, further comprising a one way valve disposed in fluid communication between said interior of said pouch and the suction mechanism,
   wherein said valve allows said fluid to be evacuated from said container but does not allow said fluid to return to said container.

11. An intra-corporeal surgical retractor according to claim 10, said valve further comprising a release mechanism which, when activated, allows said fluid to return to said pouch.

12. An intra-corporeal surgical retractor according to claim 1, further comprising an absorbent sleeve disposable around said pouch.

* * * * *